(12) United States Patent
Lee et al.

(10) Patent No.: US 7,806,859 B2
(45) Date of Patent: Oct. 5, 2010

(54) SAFETY LANCET FOR TAKING BLOOD

(75) Inventors: Cherng-Jyh Lee, Hsinchu (TW); Tzer-Ming Chen, Taipei (TW)

(73) Assignee: Eumed Biotechnology Co., Ltd. (TW)

( * ) Notice: Subject to any disclaimer, the term of this patent is extended or adjusted under 35 U.S.C. 154(b) by 324 days.

(21) Appl. No.: 12/011,174

(22) Filed: Jan. 24, 2008

(65) Prior Publication Data
US 2009/0192456 A1 Jul. 30, 2009

(51) Int. Cl.
A61M 5/00 (2006.01)
A61M 25/16 (2006.01)
A61M 25/18 (2006.01)
A61M 5/32 (2006.01)

(52) U.S. Cl. .................. 604/110; 604/533; 604/198
(58) Field of Classification Search ......... 604/192–198, 604/533, 535, 110, 111, 164.01–164.08
See application file for complete search history.

(56) References Cited

U.S. PATENT DOCUMENTS 6,293,925 B1 * 9/2001 Safabash et al. ............ 604/136
6,648,856 B1 * 11/2003 Argento ...................... 604/192
2007/0161960 A1 7/2007 Chen
2007/0162065 A1 7/2007 Li

FOREIGN PATENT DOCUMENTS

| CN | 101 036 580 A | 9/2007 |
| WO | WO 2007/050528 A | 5/2007 |

* cited by examiner

*Primary Examiner*—Nicholas D Lucchesi
*Assistant Examiner*—Rebecca E Eisenberg
(74) *Attorney, Agent, or Firm*—Jackson Walker, LLP

(57) ABSTRACT

A safety lancet for taking blood has a hollow barrel with two first slots and two second slots and a detachable needle hub. The needle hub is mounted in the barrel and has a moving base with a needle near a proximal end and a positioning base near a distal end. The positioning base detachably connects to the moving base and has a push button and two stopping resilient elements protruding symmetrically from an outer surface of the positioning base and protruding in the first slots before the push button being pushed and protruding in the second slots after the push button being pushed, so the position base can not move backward. Therefore, medical personnel are able to distinguish easily if the lancet has been used or not.

8 Claims, 6 Drawing Sheets

SAFETY LANCET FOR TAKING BLOOD

BACKGROUND OF THE INVENTION

1. Field of Invention

The present invention relates to a lancet for taking blood, and more particularly to a safety lancet that has a detachable needle hub in a barrel to prevent the safety lancet from being reused and to ensure a needle on the needle hub protrudes out of the barrel when the safety lancet is used.

2. Description of the Related Art

Generally, when medical personnel take a small amount of blood from patients or examinees, they use a lancet to pierce the patients' or examinees' skin and then take blood. Recently, the lancet that medical personnel use is disposable to prevent patients or examinees from being cross infected by the lancet.

With reference to FIG. 9, a conventional lancet comprises a hollow barrel (40), a needle hub (30) and a sheath (35). The barrel (40) has an open proximal end and an open distal end. The proximal end of the barrel (40) has a narrowed section (41). The barrel (40) near the open distal end has two slots (42). The slots (42) are defined through the barrel (40) symmetrically. The needle hub (30) is mounted slidably in the barrel (40) and has a proximal end, a distal end, an outer surface, a needle (34), a push button (31), two limiting resilient elements (33) and two stopping resilient elements (32). The needle (34) protrudes from the proximal end of the needle hub (30) and faces the proximal end of the barrel (40). The push button (31) is mounted on the distal end of the needle hub (30) and is mounted in the open distal end of the barrel (40). The limiting resilient elements (33) protrude symmetrically from the outer surface of the needle hub (30) toward the proximal end of the barrel (40) and each limiting resilient element (33) has a limiting end. The limiting end of the limiting resilient element (33) contacts the inner surface. The stopping resilient elements (32) protrude symmetrically from the outer surface of the needle hub (30) toward the distal end of the barrel (40) and correspond to the slot (34). Each stopping resilient element (32) has a stopping end. The stopping end is mounted in the slot (42) and is stopped by the distal end of the barrel (40). The sheath (35) covers the needle (34) to prevent the needle (34) from contamination and to prevent the medical personnel from piercing by the needle (34).

When using the lancet, medical personnel detach the sheath (35) from the needle (34) and then push the push button (31) toward the proximal end of the barrel (40). The needle hub (30) moves toward the narrowed section (41) of the barrel (40) and a distance between the limiting ends of the limiting resilient elements (33) is narrowed. The stopping ends of the stopping resilient elements (32) moves along the slot (42). Therefore, the needle (34) is able to protrude out of the barrel (40) to pierce a patient's or an examinee's skin and to take blood.

When thrust applied by the medical personnel is eliminated, the distance between the limiting ends of the limiting resilient elements (33) is enlarged and becomes an original distance before the push button (31) is pushed, so the needle hub (30) moves toward the distal end of the barrel (40) and allows the needle (34) to retract into the barrel (40). However, the stopping ends of the stopping resilient elements (32) move back to be stopped by the distal end of the barrel (40), so the personnel cannot distinguish if the lancet has been used or not. Accordingly, the lancet may be reused to endanger the patients or the examinees.

With reference to FIG. 10, another conventional lancet has a hollow barrel (60) and a needle hub (50). The barrel (60) has an open proximal end, an open distal end and an inner surface. The proximal end of the barrel (60) has a narrowed section (61). The inner surface of the barrel (60) near the distal end has two protrusions (63). The protrusions (63) protrude form the inner surface of the barrel (40) symmetrically. The needle hub (50) is mounted slidably in the barrel (60) and has a proximal end, a distal end, an outer surface, a needle (54), a push button (51), two limiting resilient elements (53) and two stopping resilient elements (52). The needle (54) protrudes from the proximal end of the needle hub (50) and faces the proximal end of the barrel (60). The push button (51) is mounted on the distal end of the needle hub (50) and is mounted in the distal end of the barrel (60). The limiting resilient elements (53) protrude symmetrically from the outer surface of the needle hub (30) toward the proximal end of the barrel (60) and each limiting resilient element (53) has a limiting end. The limiting end of the limiting resilient element (53) contacts the inner surface. The stopping resilient elements (52) protrude symmetrically from the outer surface of the needle hub (50) toward the distal end of the barrel (60) and each stopping resilient element (52) has a stopping end. The stopping ends are mounted between the distal end and the protrusions (63) before the lancet is used.

When using the lancet, the medical personnel push the push button (51) toward the proximal end of the barrel (60). The needle hub (50) moves toward the narrowed section (61) of the barrel (60) and a distance between the limiting ends of the limiting resilient elements (53) is narrowed. At the same time, the stopping ends of the stopping resilient elements (52) are pressed by the protrusions (63) to stride over the protrusions (63). Therefore, the needle (54) is able to protrude out of the barrel (60) to pierce a patient's or an examinee's skin and to take blood.

When thrust that applied by the medical personnel is eliminated, the distance between the limiting ends of the limiting resilient elements (53) is enlarged and becomes an original distance before the push button (51) is pushed, so the needle hub (50) moves toward the distal end of the barrel (60) and allows the needle (54) to retract into the barrel (40). The stopping ends of the stopping resilient elements (52) will be stopped by the protrusions (63), so the push button (51) cannot be re-mounted in the distal end of the barrel (60). Therefore, the personnel are able to distinguish easily if the lancet has been used or not.

However, in one aspect, when the needle hub (50) is pushed, the limiting ends of the limiting resilient elements (53) are pressed by the protrusions (63), so a degree of the thrust will be decreased and a length of the needle (54) protruding from the barrel (60) is shorter than an expected length. Consequently, the lancet may be failed to take blood from the patient or examinee. In another aspect, when the distance between the limiting resilient elements (53) is enlarged, that may cause a strong force to allow the needle hub (50) to move backward. The force may cause the stopping resilient elements (52) to be pressed by the protrusions (63) and to stride over the protrusions (63) again. Therefore, push button (51) of the needle hub (50) will be mounted in the distal end of the barrel (60) again and the needle hub (50) will move back to an original position before the push button (51) is pushed. Accordingly, the personnel still cannot distinguish if the lancet has been used or not and the lancet will still be reused to endanger the patients or the examinees.

To overcome the shortcomings, the present invention provides a safety lancet for taking blood to mitigate or obviate the aforementioned.

SUMMARY OF THE INVENTION

The primary objective of the present invention is to provide a safety lancet that has a detachable needle hub in a barrel to prevent the safety lancet from being reused and to ensure a needle on the needle hub to protrude out of the barrel when the safety lancet is used.

To achieve the objective, the safety lancet for taking blood in accordance with the present invention comprises a hollow barrel and a detachable needle hub. The barrel has two first slots and two second slots. The needle hub is mounted slidably in the barrel and has a moving base and a positioning base. The moving base is mounted near a proximal end of the barrel and has a needle. The positioning base is mounted near a distal end of the barrel, detachably connects to the moving base and has a push button and two stopping resilient elements. The stopping resilient elements protrude symmetrically from an outer surface of the positioning base and protrudes in the first slots before the push button is pushed and protrudes in the second slots after the push button is pushed, so the position base can not move backward. Therefore, medical personnel are able to distinguish easily if the lancet has been used or not.

Other objectives, advantages and novel features of the invention will become more apparent from the following detailed description when taken in conjunction with the accompanying drawings.

DETAILED DESCRIPTION OF THE INVENTION

Figure 1:
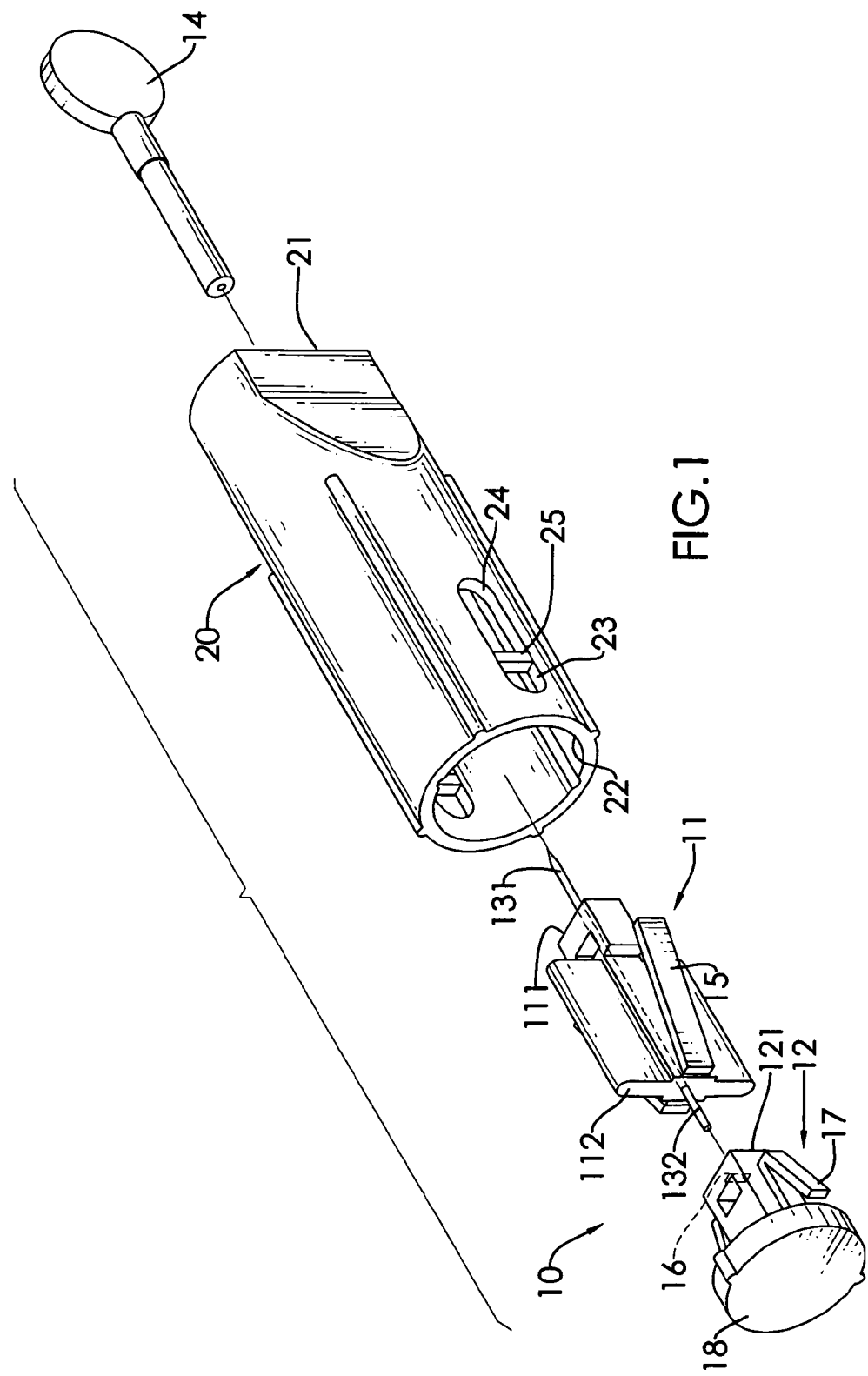
FIG. 1 is an exploded perspective view of a safety lancet for taking blood in accordance with the present invention.
Figure 2:
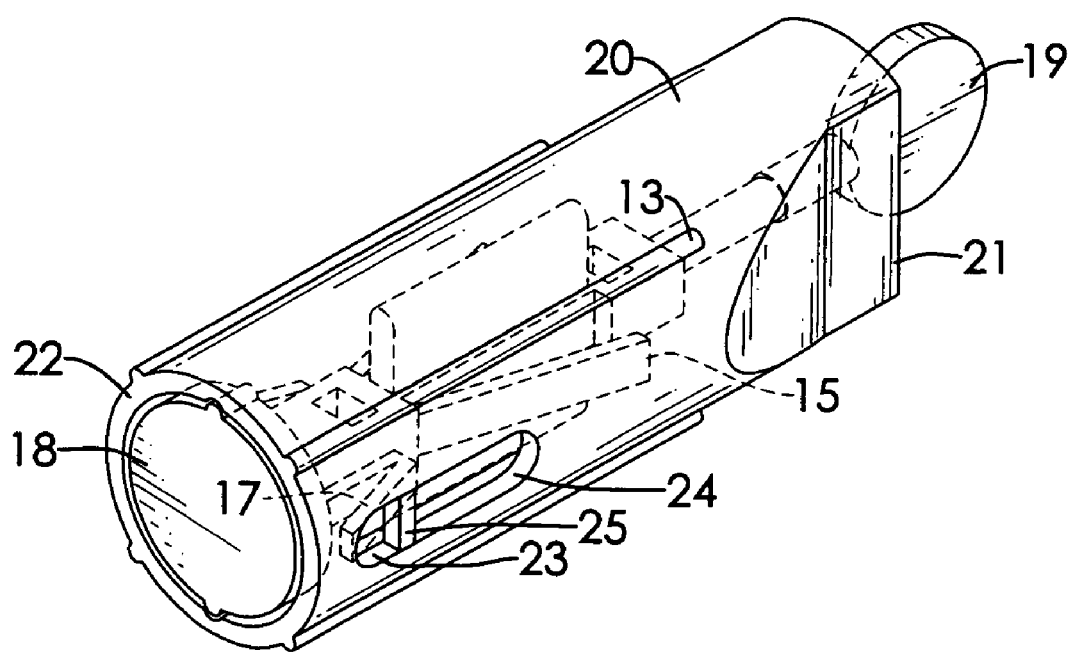
FIG. 2 is a perspective view of the safety lancet for taking blood in FIG. 1.

With reference to FIGS. 1 and 2, a safety lancet for taking blood in accordance with the present invention has a hollow barrel (20), a detachable needle hub (10) and a sheath (14).

The barrel (20) has an open proximal end (21), an open distal end (22), an inner surface, two first slots (23) and two second slots (24). The proximal end (21) of the barrel (20) has a narrowed section. The first slots (23) are symmetrically defined through the barrel (20) near the open distal end (22).

The second slots (24) are symmetrically defined through the barrel (20) far away from the distal end (22) and are respectively adjacent to the first slots (23) to form two stopping segments (25). Each stopping segment (25) is formed between the first slot (23) and the second slot (24).

The needle hub (10) is mounted slidably in the barrel (20) and has a moving base (11) and a positioning base (12).

The moving base (11) is mounted in the barrel (20) near the proximal end (21) of the barrel (20) and has a first end (111), a second end (112), an outer surface, a through hole, a needle and two limiting resilient elements (15). The first end (111) faces the proximal end (21) of the barrel (20). The second end (112) faces the distal end (22) of the barrel (20). The through hole is defined longitudinally through the moving base (11). The needle is mounted in the through hole and has a pinpoint (131) and a protruding end (132). The pinpoint (131) protrudes from the first end (111) of the moving base (11). The protruding end (132) protrudes form the second end (112) of the moving base (11). The limiting resilient elements (15) protrude symmetrically from the outer surface of the moving base (11) toward the proximal end (21) of the barrel (20) and each limiting resilient element (15) has a limiting end. The limiting ends of the limiting resilient elements (15) contact the inner surface of the barrel (20).

The positioning base (12) is mounted in the barrel (20) near the distal end (22) of the barrel (20) and has a first end (121), a second end, an outer surface, a connecting recess (16), a push button (18) and two stopping resilient elements (17). The first end (121) faces the second end (112) of the moving base (11) and contacts the second end (112) before the moving base (11) is detached from the positioning base (12). The second end faces the distal end (22) of the barrel (20). The connecting recess (16) is formed in the first end (121) of the positioning base (12) and holds the protruding end (132) of the needle before the moving base (11) is detached from the positioning base (12). The push button (18) is mounted on the second end of the positioning base (12) and allows medical personnel to push the position base (12). The stopping resilient elements (17) protrude symmetrically from the outer surface of the positioning base (12) toward the proximal end (21) of the barrel (20) and each stopping resilient element (17) has a stopping end. The stopping ends of the stopping resilient element (17) has an original position with the stopping ends extending respectively in the first slots (23) before the push button (18) is pushed and a final position with the stopping ends extending respectively in the second slots (24) after the push button (18) is pushed.

The sheath (14) detachably covers the pinpoint (131) of the needle to prevent the needle from contamination and to prevent the medical personnel from piercing by the needle.

Figure 3:
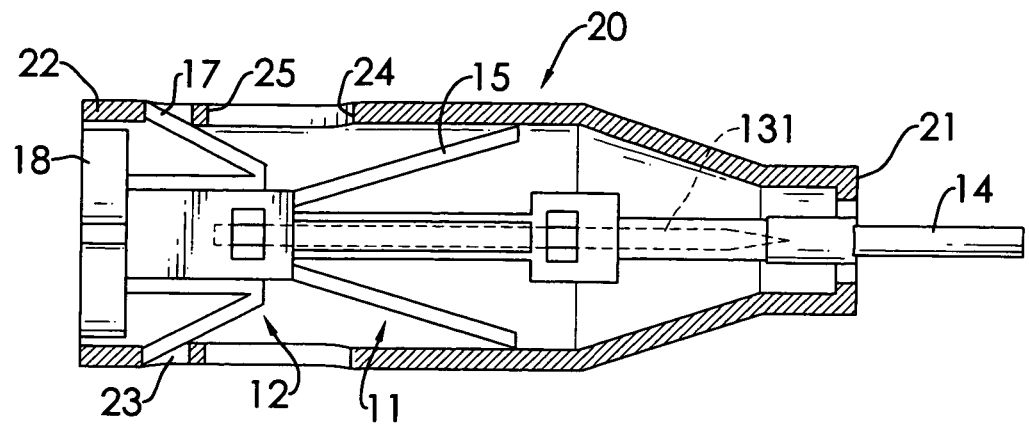
FIG. 3 is a cross sectional side view of the safety lancet for taking blood in FIG. 1 before the safety lancet is used.

With further reference to FIG. 3, when using the lancet, the medical personnel detach the sheath (14) from the needle. At this time, the limiting ends of the limiting resilient elements (15) protrude in the first slots (23).

Figure 4:
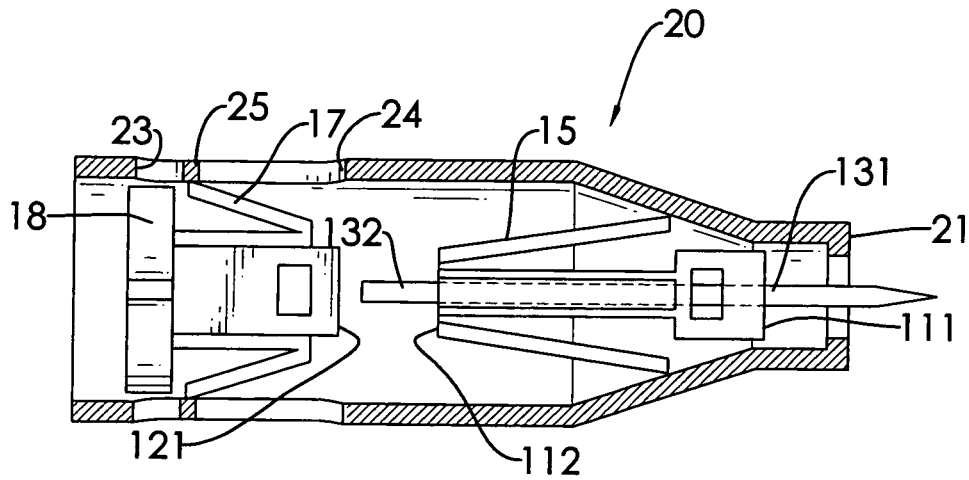
FIG. 4 is an operational cross sectional side view of the safety lancet for taking blood in FIG. 3 during the safety lancet is used.

With further reference to FIG. 4, then the medical personnel push the push button (18) toward the proximal end (21) of the barrel (20). The needle hub (20) moves toward the narrowed section of the barrel (20). A distance between the limiting ends of the limiting resilient elements (15) is narrowed when the moving base (11) moves in the narrow section. A distance between the stopping ends of the stopping resilient elements (17) is narrowed when the stopping ends stride over the stopping segments (25). Then, the limiting ends of the limiting resilient elements (15) stride over the stopping segments (25) and extend respectively in the second slots (24), so the position base (12) stops moving. Meanwhile, the moving base (11) keeps moving toward the proximal end (21) of the barrel (20) to allow the pinpoint (131) of the needle to protrude out of the barrel (20) and to pierce a patient's or an examinee's skin and to take blood.

Figure 5:
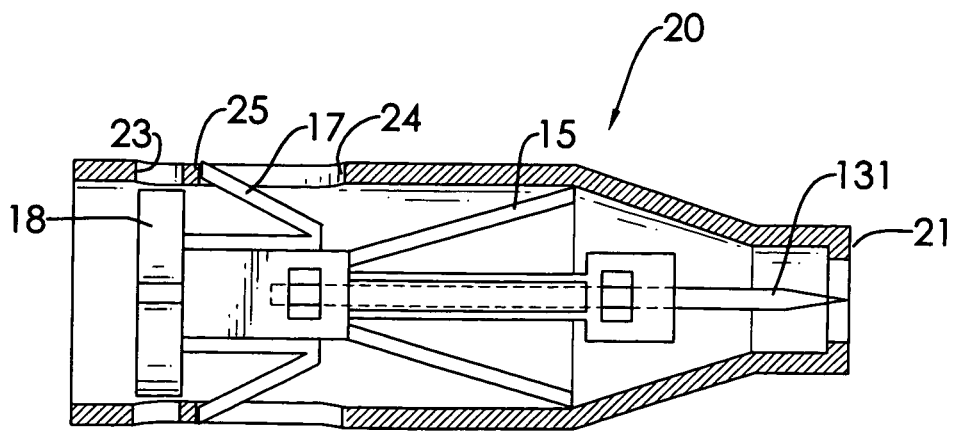
FIG. 5 is an operational cross sectional side view of the safety lancet for taking blood in FIG. 4 after the safety lancet is used.

With further reference to FIG. 5, after the needle took blood, thrust that applied by the medical personnel is eliminated, the distance between the limiting ends of the limiting resilient elements (15) is enlarged and becomes an original distance before the moving base (11) moves in the narrow section, so the needle hub (10) moves toward the distal end (22) of the barrel (20) and allows the needle to retract into the barrel (20).

Because the stopping ends of the stopping resilient elements (17) protrude in the second slot (24), the position base (12) can not move toward the distal end (22) of the barrel (20) and the push button (18) cannot be re-mounted in the distal end (22) of the barrel (20) anymore. Even if the moving base (11) retracts to press against the position base (12), the second slot (24) can hold firmly the stopping ends of the stopping resilient elements (17) and the stopping segments (25) can stop the stopping ends from moving backward. Therefore, the medical personnel are able to distinguish easily if the lancet has been used or not.

Moreover, the needle hub (10) is detachable, so although the position base (12) stopped by the stopping segments (25), the moving base (11) still keeps moving toward the proximal end (21) of the barrel (20) by inertia. Accordingly, the pinpoint (131) of the needle is able to protrude with an enough length to take blood.

Figure 6:
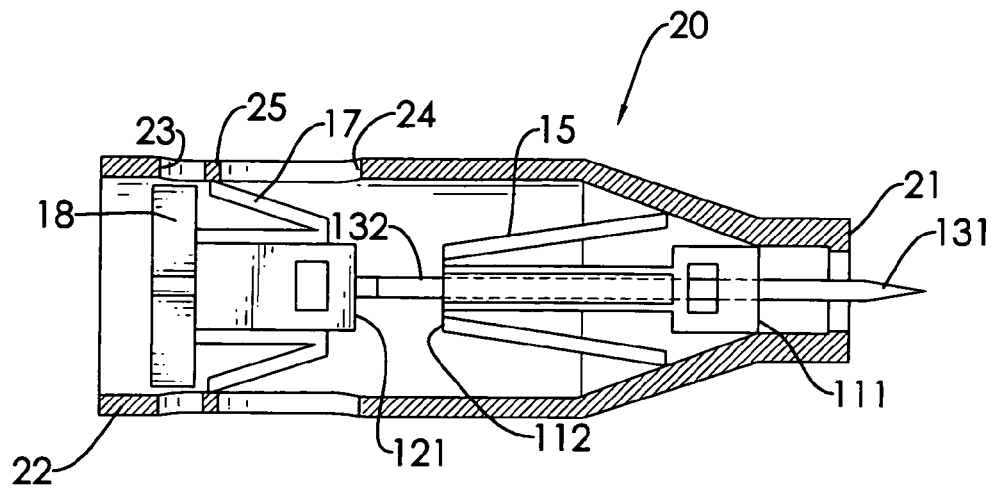
FIG. 6 is a cross sectional side view of the safety lancet for taking blood in FIG. 1 with an narrow section of a barrel having an increased thickness.

With further reference to FIG. 6, a thickness of the narrow section of the barrel (20) may be changed to adjust a length that the pinpoint (131) of the needle protrudes out of the barrel (20). When the thickness of the narrow section is thin, the length that the pinpoint (131) protrudes out of the barrel (20) is long. When the thickness of the narrow section is thick, the length that the pinpoint (131) protrudes out of the barrel (20) is short.

Figure 7:
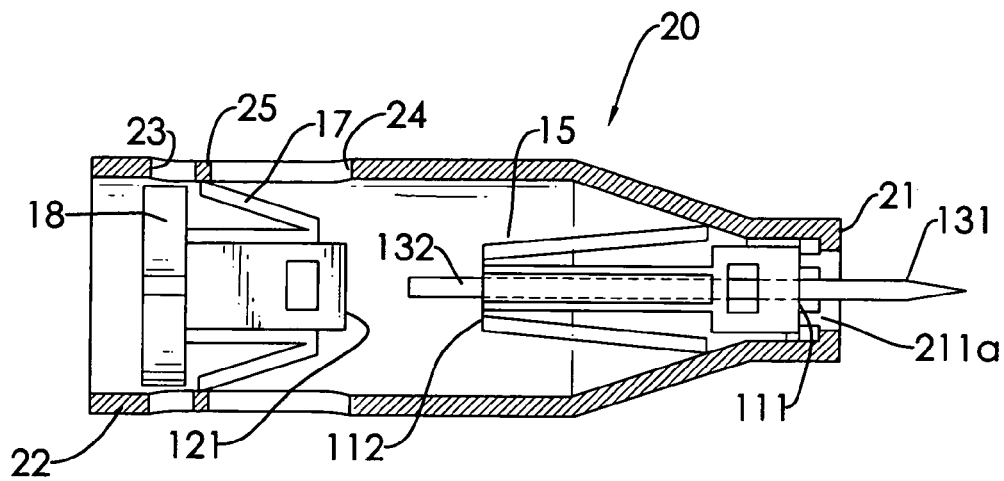
FIG. 7 is a cross sectional side view of the safety lancet for taking blood in FIG. 1 with a short limiting protrusion in a barrel.
Figure 8:
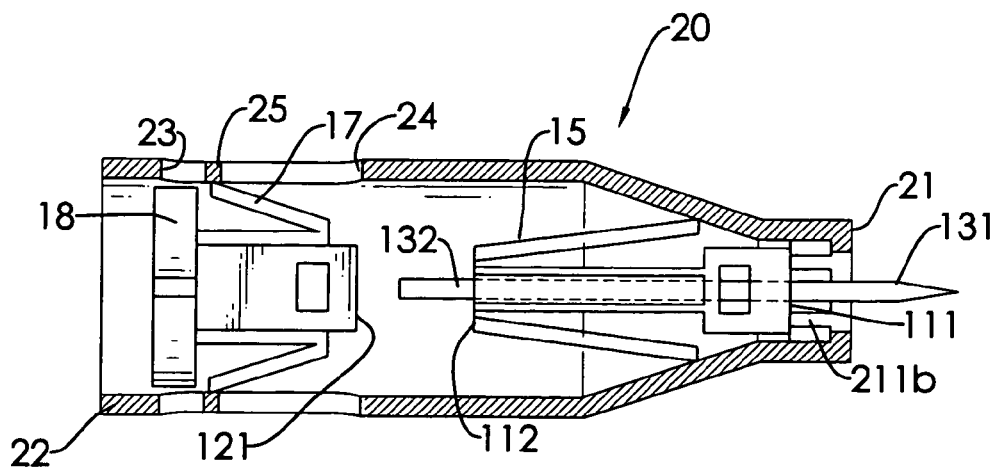
FIG. 8 is a cross sectional side view of the safety lancet for taking blood in FIG. 1 with a long limiting protrusion in a barrel.
Figure 9:
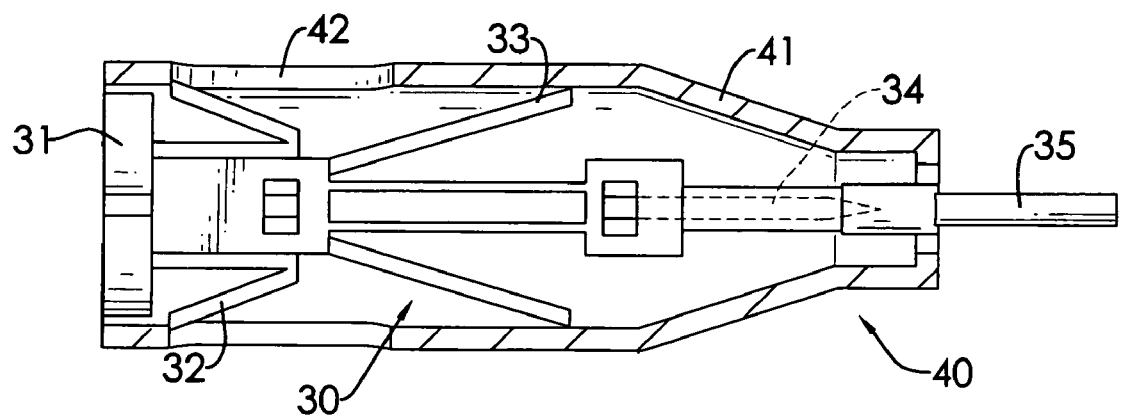
FIG. 9 is a cross sectional side view of a conventional lancet for taking blood in accordance with the prior art.
Figure 10:
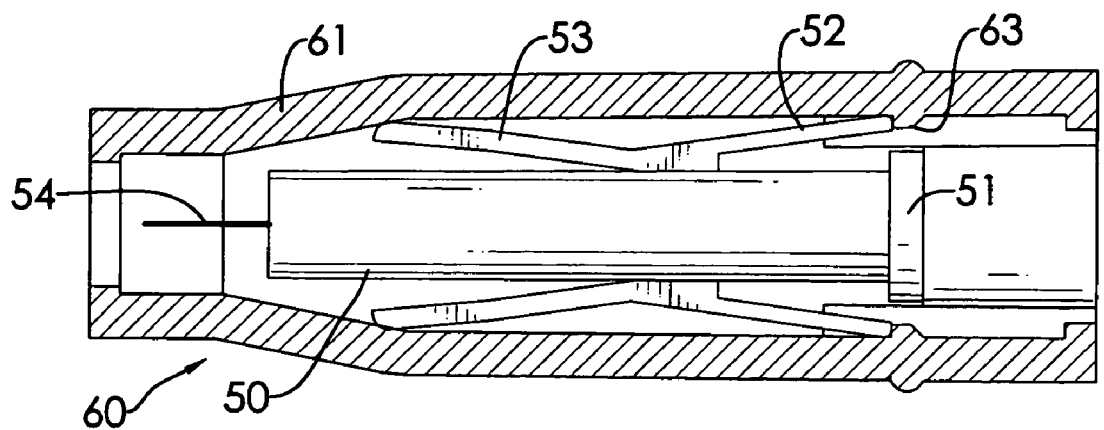
FIG. 10 is a cross sectional side view of another conventional lancet for taking blood in accordance with the prior art.

With further reference to FIGS. 7 and 8, the barrel (20) further has at least one limiting protrusion. The at least one limiting protrusion (211a, 211b) is mounted in the barrel (20), abuts the proximal end (21) of the barrel (20) and stops the moving base (11) from moving forward. Therefore, a length of the at least one limiting protrusion is able to adjust the length that the pinpoint (131) of the needle protrudes out of the barrel (20). When the barrel (20) has at least one short limiting protrusion (211a), the length that the pinpoint (131) protrudes out of the barrel (20) is long. When the barrel (20) has at least one long limiting protrusion (211b), the length that the pinpoint (131) protrudes out of the barrel (20) is short.

Even though numerous characteristics and advantages of the present invention have been set forth in the foregoing description, together with details of the structure and function of the invention, the disclosure is illustrative only. Changes may be made in detail, especially in matters of shape, size and arrangement of parts within the principles of the invention to the full extent indicated by the broad general meaning of the terms in which the appended claims are expressed.

What is claimed is:

1. A safety lancet for taking blood comprising:
  a hollow barrel having
    an open proximal end having a narrowed section;
    an open distal end;
    an inner surface;
    two first slots being symmetrically defined through the barrel near the distal end; and
    two second slots being symmetrically defined through the barrel far away from the distal end and being respectively adjacent to the first slots to form two stopping segments and each stopping segment being mounted between the first slot and the second slot; and
  a detachable needle hub being mounted slidably in the barrel and having
    a moving base being mounted in the barrel near the proximal end of the barrel and having
      a first end facing the proximal end of the barrel;
      a second end facing the distal end of the barrel;
      an outer surface;
      a through hole being defined longitudinally through the moving base;
      a needle being mounted in the through hole; and
      two limiting resilient elements protruding symmetrically from the outer surface of the moving base toward the proximal end of the barrel and each limiting resilient element having a limiting end contacting the inner surface of the barrel;
    a positioning base being mounted in the barrel near the distal end of the barrel and having
      a first end facing the second end of the moving base and contacting the second end before the moving base being detached from the positioning base;
      a second end facing the distal end of the barrel;
      an outer surface;
      a push button being mounted on the second end of the positioning base; and
      two stopping resilient elements protruding symmetrically from the outer surface of the positioning base toward the proximal end of the barrel and each stopping resilient element having a stopping end that having an original position with the stopping ends extending respectively in the first slots and a final position with the stopping ends extending respectively in the second slots.

2. The safety lancet for taking blood as claimed in claim 1, wherein
  the needle has
    a pinpoint protruding from the first end of the moving base; and
    a protruding end protruding form the second end of the moving base; and
  the positioning base further has a connecting recess being formed in the first end of the positioning base and holding the protruding end of the needle before the moving base being detached from the positioning base.

3. The safety lancet for taking blood as claimed in claim 1 further has a sheath detachably covering needle.

4. The safety lancet for taking blood as claimed in claim 2 further has a sheath detachably covering the pinpoint.

5. The safety lancet for taking blood as claimed in claim 1, wherein the barrel further has at least one limiting protrusion being mounted in the barrel, abutting the proximal end of the barrel and stopping the moving base from moving forward.

6. The safety lancet for taking blood as claimed in claim 2, wherein the barrel further has at least one limiting protrusion being mounted in the barrel, abutting the proximal end of the barrel and stopping the moving base from moving forward.

7. The safety lancet for taking blood as claimed in claim 3, wherein the barrel further has at least one limiting protrusion being mounted in the barrel, abutting the proximal end of the barrel and stopping the moving base from moving forward.

8. The safety lancet for taking blood as claimed in claim 4, wherein the barrel further has at least one limiting protrusion being mounted in the barrel, abutting the proximal end of the barrel and stopping the moving base from moving forward.

* * * * *